United States Patent [19]

Leviton et al.

[11] Patent Number: 4,487,606
[45] Date of Patent: Dec. 11, 1984

[54] SUCTION CANISTER WITH SHUT-OFF VALVE AND SMOKE FILTER

[75] Inventors: Jan L. Leviton, E. Brunswick; Charles E. Meisch, Hasbrouck Heights, both of N.J.

[73] Assignee: Becton, Dickinson and Company, Paramus, N.J.

[21] Appl. No.: 462,502

[22] Filed: Jan. 31, 1983

[51] Int. Cl.³ .............................................. A61M 1/00
[52] U.S. Cl. .................................... 604/319; 141/59; 55/385 C; 55/482
[58] Field of Search .............................. 604/317–320; 141/59, 61; 137/205; 433/91; 55/385 C, 527, 528, 482, 486, 487

[56] References Cited

U.S. PATENT DOCUMENTS

| | | | |
|---|---|---|---|
| 3,719,197 | 3/1973 | Pannier et al. | 137/205 |
| 3,738,381 | 6/1973 | Holbrook | 137/199 |
| 4,013,076 | 3/1977 | Puderbaugh et al. | 128/276 |
| 4,111,204 | 9/1978 | Hessel | 128/276 |
| 4,228,798 | 10/1980 | Deaton | 128/276 |
| 4,275,732 | 6/1981 | Gereg | 604/320 |
| 4,323,082 | 4/1982 | Helms et al. | 131/281 |

OTHER PUBLICATIONS

"Gore-Tex ®", Expanded PTFE, W. L. Gore & Associates, Inc., Elkton, Maryland 21921, 1978.
"Gore-Tex ®", A Porous and Versatile Structure of Fluon ® PTFE, W. L. Gore & Associates, Inc., Elkton, Maryland 21921.
Gore-Tex Membrane Products, W. L. Gore & Associates, Inc., Elkton, Maryland 21921.

Primary Examiner—C. Fred Rosenbaum
Assistant Examiner—J. L. Kruter
Attorney, Agent, or Firm—John L. Voellmicke

[57] ABSTRACT

A suction canister assembly comprises an enclosed receptacle having a first opening for providing suction to the receptacle and a second opening for drawing fluids, including liquids and gases, into the receptacle during suction. A unitary shut-off valve/filter element is associated with the interior side of the first opening. This element is oriented within the receptacle so as to be contacted by liquid in the receptacle which rises therein. The element is porous and is adapted to filter particulate matter from gas passing therethrough. In addition, the valve/filter element is capable of developing sufficiently high surface tension under liquid contact to serve as a barrier against liquid passage therethrough at pressure differentials across the element when vacuum is applied on one side of the element. As a result, the element is adapted to terminate suction through the suction opening when liquid rises in the receptacle to completely cover the element. A smoke filter element for filtering solids and liquids contained in smoke is positioned adjacent to the valve/filter element. A spacer for substantially preventing filtered matter collected by the smoke filter from migrating to the valve/filter element is positioned between the valve/filter element and the smoke filter.

24 Claims, 10 Drawing Figures

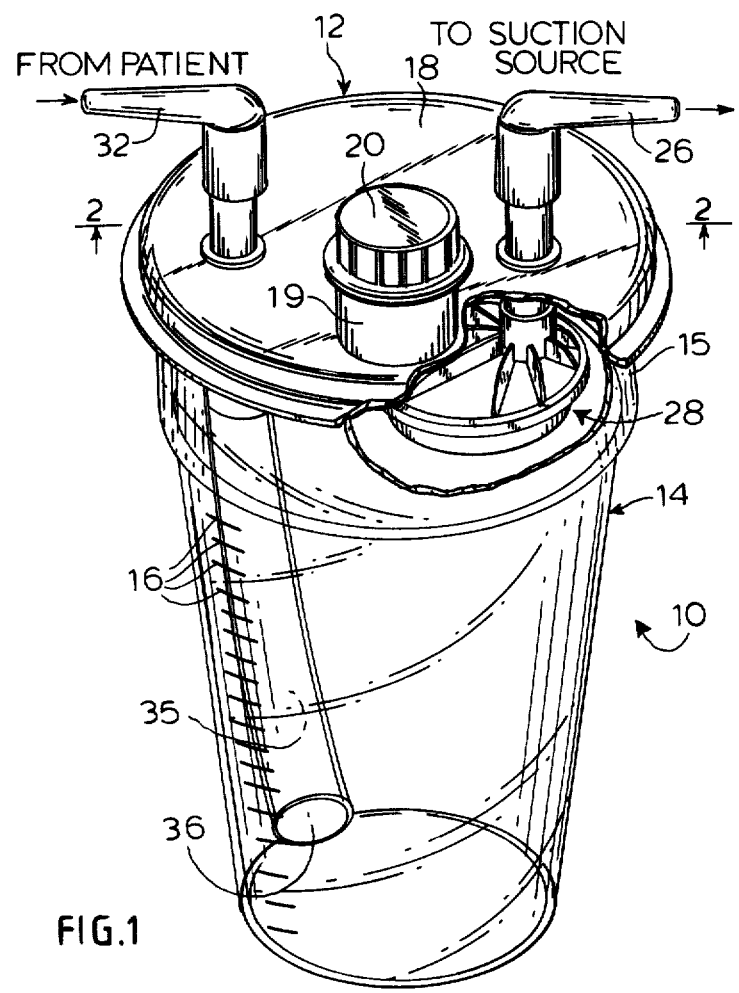

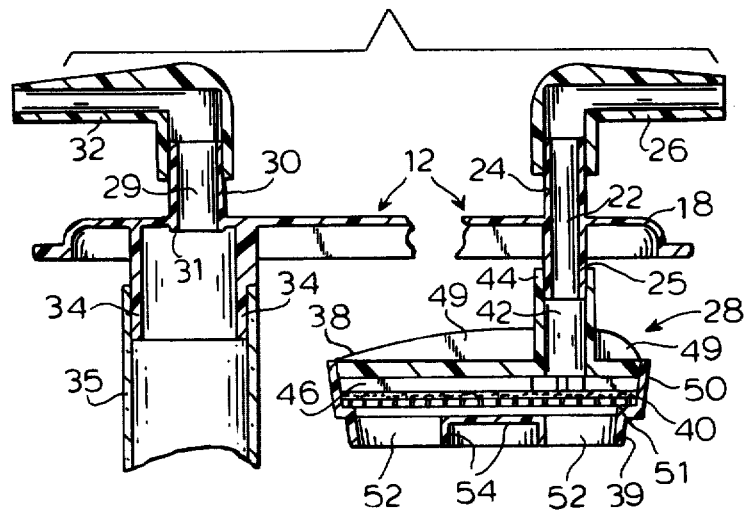
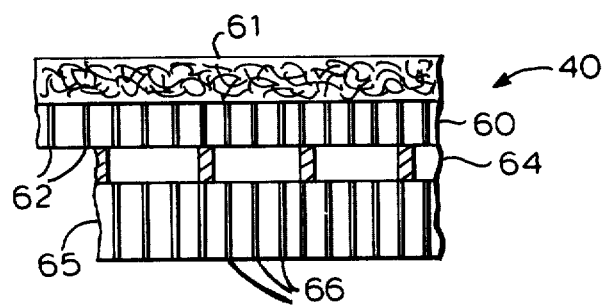

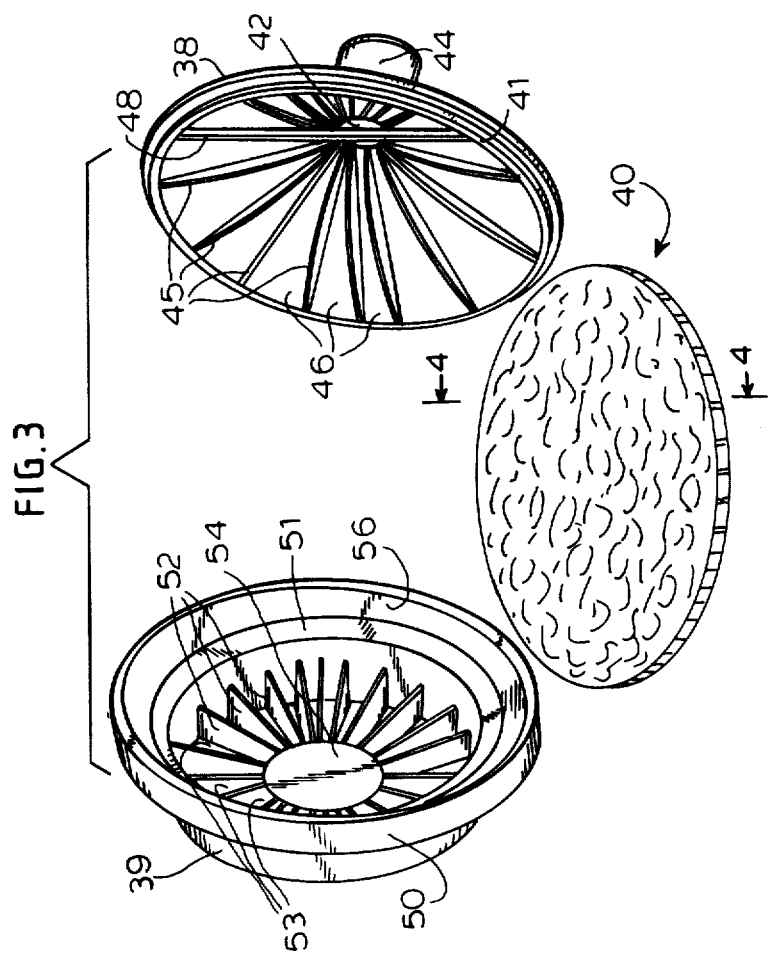

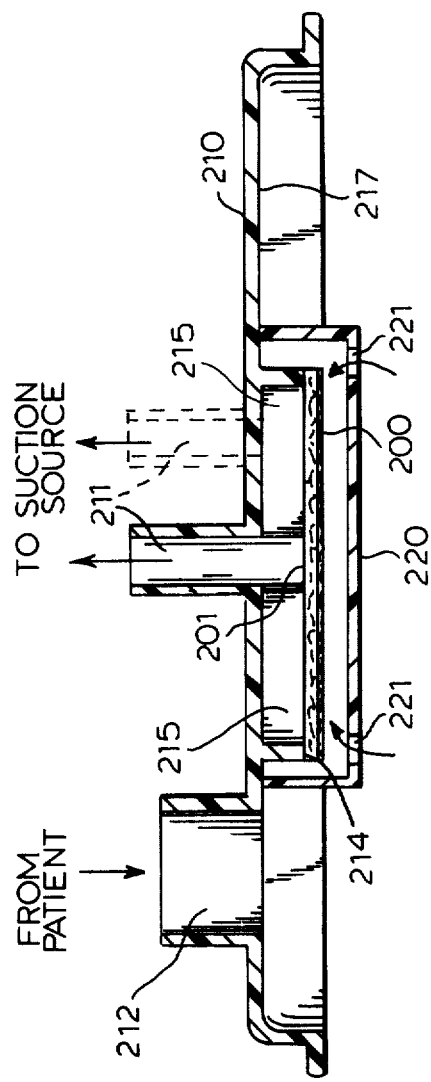

SUCTION CANISTER WITH SHUT-OFF VALVE AND SMOKE FILTER

BACKGROUND OF THE INVENTION

1. Field of the Invention

The present invention relates to a suction canister, and more particularly, concerns a suction canister used for withdrawing and collecting body fluids from a patient during surgical procedures.

2. Description of the Prior Art

Suction canisters are employed in the hospital environment, and particularly during surgical procedures, to drain body liquids from a patient. In general, suction canisters employ a collection system and a vacuum source, such as a pump, to facilitate this drainage procedure. The canister generally includes a flexible line or hose connected to the vacuum source so that vacuum can be applied to the interior of the canister. Another flexible line or hose extends from the canister to the source of body liquids in the patient. Once the vacuum is applied, a negative pressure gradient is communicated through the interior of the suction canister so that body liquids are drawn into the canister.

As the suction canister fills, a need for controlling overflow has been recognized. To this end, a number of prior suction canister devices have employed shut-off valves to control any overflow of liquid from the canister. More particularly, previous devices have employed hydrophobic filters to prevent the passage of liquid out of the suction canister during operation. U.S. Pat. Nos. 3,719,197; 3,738,381; 4,013,076; 4,111,204 and 4,275,732 disclose suction canisters wherein the use of hydrophobic material is employed for liquid control purposes. U.S. Pat. Nos. 4,111,204 and 4,275,732 both use a hydrophobic material in conjunction with a filter bag disposed inside the suction canister.

In addition to the control of liquid overflow, suction canister systems have also been concerned with particulate matter control, including bacteria. U.S. Pat. No. 4,228,798, discloses a medical suction system with a hygroscopic filter sufficient to filter bacteria having dimensions less than about five microns from the airstream developed during the suctioning process. Other filter materials are known to remove bacteria and particulate matter from medical gases. For example, W. L. Gore and Associates, Inc., of Elkton, Md., makes filters known as GORE-TEX ® membranes and laminates to vent air while preventing fluid leakage or bacterial entry. Descriptions of these membranes and laminates are found in three W. L. Gore and Associates, Inc. publications, entitled, "GORE-TEX Membrane Products" (1980); "GORE-TEX Expanded PTFE" (1978); and "GORE-TEX Expanded PTFE" (an ICI Engineering Plastics publication reprint, No. 4, 1975). U.S. Pat. No. 4,187,390 also describes some of these filter materials. The Applicants are also familiar with the particulars of U.S. Pat. Application Ser. No. 241,153, filed Mar. 6, 1981, now abandoned, and a continuation application thereof Ser. No. 494,745, filed May 16, 1983, the details of both applications of which are incorporated herein by reference, and which disclose a suction canister assembly using a unitary shut-off valve, filter element located within the interior of a rigid suction canister.

The use of surgical tools such as lasers and electric knives in surgical procedures is increasing. Both of these tools minimize bleeding by cauterizing while cutting tissue and both have a tendency to produce smoke which may sometimes be dense. This smoke creates problems for suction canisters using hydrophobic filters as valves since it has the ability to rapidly shut down the valve regardless of the amount of fluid collected in the canister. Therefore, it is necessary to filter out this smoke before it can reach the hydrophobic filter. It is also necessary to filter this smoke since it contains proteinized vapors which, if they get through the filter, can contaminate the apparatus and areas downstream from the filter by providing a growth media for bacteria.

While body liquid control and particulate matter filtration, including bacteria, have been addressed by the prior art in suction canister systems, the prior art has not addressed the problem of smoke filtration. There is still a need for a straightforward, easily fabricated system which can adequately filter smoke and other particulate matter including bacteria while controlling liquid overflow. In addition, it is also desirable that the mechanism for controlling liquid overflow also be capable of shutting down the vacuum system which draws liquid into the suction canister. It is to these ends that the present invention is directed.

SUMMARY OF THE INVENTION

The suction canister assembly of the present invention comprises an enclosed receptacle having a first opening for providing suction to the receptacle and a second opening for drawing fluids, including liquids and gases, into the receptacle during suction. Unitary shut-off valve/filter means is associated with the interior side of the first opening and is adapted to lie substantially parallel to the free upper surface of liquid which enters the receptacle. The valve/filter means is oriented within the receptacle to be contacted by liquid in the receptacle which rises therein. The valve/filter means is porous and is adapted to filter particulate matter from gas passing therethrough, and is capable of developing sufficiently high surface tension under liquid contact to serve as a barrier against liquid passage therethrough at pressure differentials across the valve/filter means when vacuum is applied to one side of the element, with normal atmospheric pressure conditions on the opposite side. With such structure, the valve/filter means is adapted to terminate suction through the suction opening when liquid rises in the receptacle to completely cover the element. Smoke filter means for filtering solids and liquids contained in smoke is positioned adjacent to the valve/filter means on the side of the valve/filter means which is opposite the interior side of the first opening. Connection means is provided for securing the valve/filter means and the smoke filter means together in an air-tight arrangement so that gases leaving the suction canister must pass through the smoke filter means and the valve/filter means before passing through the first opening.

In accordance with another embodiment of the present invention, the suction canister assembly comprises a cup-shaped receptacle having an open mouth portion. A cover is sealably connected to the receptacle over the mouth portion, with the cover having a suction opening therethrough for communicating with a source of vacuum applied to the exterior side of the suction opening. A liquid passage opening extends through the cover for communicating with a source of liquid exterior to the canister so that liquid is passable therethrough to enter the receptacle under suction conditions provided through the suction opening by the vacuum source. An upper housing portion projects downwardly from the cover into the receptacle terminating at a generally planar surface which is adapted to be substantially parallel to the free upper surface of the liquid which enters the receptacle. The upper housing portion surrounds the suction opening and defines an interior portion which is in fluid communication with the suction opening. A unitary shut-off valve/filter element is positioned adjacent to and contacts the planar surface. This element is adapted to be contacted by liquid in the receptacle which rises to a predetermined level. The element is porous with a maximum pore rating of about 0.5 microns for filtering particulate matter including microorganisms from gas passing therethrough. Furthermore, the valve/filter element is capable of developing sufficiently high surface tension under liquid contact to serve as a barrier against liquid passage therethrough at pressure differentials across the element up to 14.7 psi (1,034 g/cm$^2$). This element is further adapted to terminate suction through the suction opening at suction pressures up to 14.7 psi (1,034 g/cm$^2$) when liquid rises in the receptacle to completely cover the element. Smoke filter means for filtering solids and liquids contained in smoke is positioned adjacent to the filter element on the side opposite the planar surface. Spacer means for substantially preventing filtered matter collected by the smoke filter means from migrating to the filter element is interposed between the filter element and the smoke filter means. A lower housing including a side wall, a bottom portion and a generally planar shoulder extending inwardly from the side wall is provided. The side wall and the bottom portion define an interior cavity of the lower housing. This side wall is attached to the upper housing and positioned so that the planar surface and the shoulder are in a substantially parallel relationship holding the filter element, the spacer means and the smoke filter means therebetween in an air-tight seal around the periphery thereof. The bottom portion contains a plurality of apertures adapted to allow gases to flow freely therethrough.

In still another embodiment of the present invention, the shut-off valve/filter element is laminated to a thin porous backing sheet adapted to provide strength and stability to the composite structure of the valve/filter element and backing sheet. This composite structure is connected to the planar surface of the upper housing portion so that the element faces the interior of the receptacle so as to be contacted by the liquid therein. Smoke filter means for filtering solids and liquids contained in smoke is positioned adjacent to the filter element on the side opposite the planar surface. Spacer means for substantially preventing filtered matter collected by the smoke filter means from migrating to the filter element is interposed between the filter element and the smoke filter means. The spacer means is laminated to the filter element on the side opposite the backing sheet and the smoke filter means is laminated to the spacer means.

In accordance with the principles of the present invention, the unitary shut-off valve/filter element combines two functions into one. It filters particulate matter, including bacteria, during the suction process and also serves as a shut-off valve to terminate suction through the suction opening when liquid rises in the receptacle to cover the element. In this invention, the valve/filter element not only controls liquid overflow in the canister, but serves to shut down the source of vacuum which is applied to the contents inside the canister. The present invention also provides a smoke filter for filtering solids and liquids contained in smoke generated by surgical tools such as lasers and electric knives.

This smoke, if not effectively filtered, would contaminate the shut-off valve causing it to terminate suction through the suction opening before liquid in the receptacle contacts the element. Accordingly, the present invention provides a straightforward, easily fabricated system which can adequately filter smoke and other particulate matter including bacteria while controlling liquid overflow and having the capacity to shut down the vacuum system only when liquid in the suction canister contacts the shut-off valve. Other features of the various embodiments of the invention as mentioned above, will be pointed out in the ensuing detailed description.

BRIEF DESCRIPTION OF THE DRAWINGS

FIG. 1 is a perspective view of the preferred embodiment of the suction canister assembly of the present invention;

FIG. 2 is a cross-sectional view of the cover assembly of FIG. 1 taken along line 2—2 thereof;

FIG. 3 is an exploded perspective view of the components of the valve/filter housing assembly of FIG. 1;

FIG. 4 is an enlarged cross-sectional view of the composite valve/filter assembly taken along line 4—4 of FIG. 3;

FIG. 10 is a cross-sectional view of the cover of FIG. 9 taken along line 10—10 thereof and also showing cross-sectional views of the composite valve/filter assembly and the splash shield as assembled.

DETAILED DESCRIPTION

Figure 5:
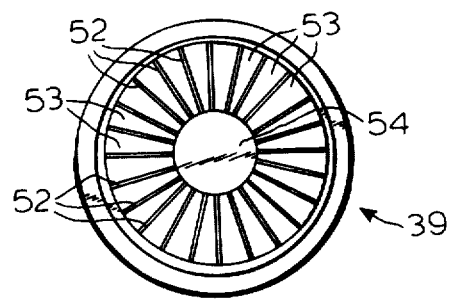
FIG. 5 is a bottom plan view of the valve/filter housing of FIG. 1.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

Adverting to the drawings, and FIG. 1 in particular, there is illustrated a suction canister assembly 10. Suction canister assembly 10 preferably is composed of two major components: a cover assembly 12 and a receptacle 14. The receptacle is preferably made of clear, rigid plastic material, and is cupshaped with an open mouth portion 15. A plurality of gradation marks 16 may be included around the periphery of the cylindrically-shaped receptacle in order to provide the user with an indication of volume of liquid collected. Typical suction canisters may hold a volume of 1,000–1,500 cubic centimeters. However, these volumes may vary according to choice and depending upon the intended use of the suction canister.

Cover assembly 12 is more clearly illustrated in FIG. 2, taken in conjunction with FIG. 1. As can be seen in these drawings, cover assembly 12 includes a cover 18 which is preferably circularly-shaped and is intended to sealably fit over mouth portion 15 of receptacle 14. The fit between cover 18 and receptacle 14 should be sufficiently airtight so that a vacuum can be applied to the inside of the receptacle without leakage around the rim of mouth portion 15 where it contacts cover 18. A sufficiently tight snap-fit not only allows assembly of the cover assembly to the receptacle, but also is generally adequate for sealing the receptacle during vacuum conditions. Cover 18 may include a pour spout 19 with a removable lid 20 covering same. This, of course, will allow liquid inside the receptacle to be poured therefrom, if desired.

A suction opening 22 extends through cover 18 defined by an upper post 24 on the exterior side of the cover and a lower post 25 on the interior side of the cover. A hollow elbow connector 26 is connected to post 24. A tube or other flexible line (not shown) extends between connector 26 and a suction source, such as a pump, in order to provide a source of vacuum through suction opening 22. Connected to post 25 on the interior side of cover 18 is a valve/filter housing 28, illustrated in FIGS. 1 and 2 in its preferable form, the details of which will be discussed hereinbelow.

Cover 18 also includes a liquid passage opening 29 therethrough, defined by an upper post 30 on the exterior side of the cover and a short lower post 31 on the interior side of the cover. Connected to upper post 30 is a hollow connector 32 similar in all respects to connector 26 hereinbefore described. A tube or flexible line (not shown) is connected to connector 32 and extends to a source of body liquid, such as found in a patient undergoing a surgical operation. Surrounding short lower post 31 on the interior side of cover 18 is a longer lower post 34. Connected to longer lower post 34 and extending downwardly is a flexible sheath 35, preferably transparent. This sheath depends deep into receptacle 14 and includes an opening 36 at its distal end. As liquid from the body source passes through liquid passage 29 it is funneled through sheath 35 directly toward the bottom of the receptacle. Therefore, sheath 35 serves as a splash guard or the like in order to prevent body liquids from splashing directly against the valve/filter housing. This sheath is merely a preferred feature and is not essential to the operation of the canister assembly. In essence, once the vacuum source is connected to connector 26, a negative pressure gradient is communicated to the inside of the receptacle 14. This suction, in turn, draws liquid from the source in the patient through liquid passage opening 29 for collection of this liquid inside the receptacle. These features of a suction canister system, in general, are well known.

Turning now to FIGS. 3, 4 and 5, taken together with FIGS. 1 and 2, the details of preferred valve/filter housing 28 are illustrated. Housing 28 includes an upper portion 38 and a lower portion 39, both enclosing the preferred composite valve/filter assembly 40 within. Referring to upper portion 38, it includes a generally planar surface 41 preferably circularly-shaped. A hole 42 extends through the planar surface, and is defined by an upwardly extending post 44. This post is connected to lower post 25 on the interior side of cover 18 so that the inside of housing 28 is in fluid communication with suction opening 22. Both hole 42 and upwardly extending post 44 are offset from the center of upper portion 38 to allow the housing to be connected to post 25 without interfering with the wall of receptacle 14. This is due to the fact that suction opening 22 extends through cover 18 toward the outside periphery thereof. It is preferred that upwardly extending post 44 of upper portion 38 be removably connected to lower post 25 using an interference fit between the outside diameter of post 25 at the inside diameter of post 44. Permanent connection of post 25 at post 44 using adhesive or other suitable means is also within the purview of this invention.

On the under or interior side of planar surface 41 is a plurality of ribs 45, spaced from each other and preferably extending radially from hole 42 and terminating at the outside rim of the planar surface. Between adjacent ribs 45 are channels 46, each channel being in fluid communication with hole 42. One rib 48 extends across hole 42 to provide support to the composite valve/filter assembly as hereinafter described. On the outside surface of upper portion 38 is a plurality of structural stiffeners 49 which provide additional transverse rigidity to the upper portion.

Referring now to lower portion 39, it is substantially cylindrically-shaped including a cup portion 50, a shoulder 51 and annular interior side wall 56. As can be seen particularly in FIG. 2, both composite valve/filter assembly 40 and planar surface 41 of the upper portion are sized to fit within cup portion 50 to rest on shoulder 51. It is preferable that the upper and lower portions of housing 28 be sealed together such as by heat sealing (if thermoplastic materials are used), adhesives, mechanical wedging or the like. The bottom surface of lower portion 39 is defined by a plurality of spaced, radially directed spokes 52, with a space 53 between adjacent spokes. These spokes provide transverse rigidity to the bottom surface of the lower portion. The spokes are connected at their interior ends to a hub 54. Space 53 between spokes 52 provides sufficient open space within this framework for allowing liquids and gases to enter the housing. The spokes also prevent damage to the composite valve/filter assembly inside especially during handling, shipment and usage.

When composite valve/filter assembly 40 is placed between upper portion 38 and lower portion 39 of the housing, it overlies ribs 45 on the upper portion. During suction, the pressure gradient tends to draw the valve/filter element upwardly; ribs 45 then serve to prevent the valve/filter element from totally collapsing against planar surface 41, whereas rib 48 serves to prevent the composite valve/filter assembly from being sucked into hole 42. Gases which pass through composite valve/filter assembly 40 enter channels 46 which communicate with hole 42. Therefore, the support provided by the rib structure provides adequate gas passage through the composite valve/filter assembly during the suction procedure. Before turning to the details of the composite valve/filter assembly, FIGS. 1 and 2 illustrate the preferred orientation of the valve/filter housing, and particularly the composite valve/filter assembly within. In this embodiment, the composite valve/filter assembly is oriented to be substantially parallel to the free upper surface of liquid which enters the receptacle; in this configuration, composite valve/filter assembly 40 is thus in a substantially horizontal position. The function of this embodiment will be described more fully hereinafter in conjunction with FIG. 6.

Referring now more specifically to FIGS. 3 and 4, the preferred composite valve/filter assembly 40 is illustrated. Composite assembly 40 includes a unitary shut-off valve/filter element 60, and in preferable embodiments of the present invention, a thin porous backing sheet 61 laminated to element 60. A spacer 64 is laminated to element 60 and a prefilter 65 is laminated to the spacer to complete the preferred composite valve/filter assembly structure.

Backing sheet 61 improves the structural integrity of the composite valve/filter assembly. In the preferred embodiment the backing sheet also provides a surface for heat sealing or adhesively bonding the element to ribs 45 and planar surface 41 in an air tight arrangement so that all gases flowing from the interior of the canister through suction opening 22 pass through composite assembly 40 and not around it.

Valve/filter element 60 is preferably a thin porous membrane which includes a plurality of pores 62 therethrough illustrated in FIG. 4 in graphic form. It is appreciated that those skilled in the art will recognize that pores 62 may not extend straight through the thickness of the valve/filter element material; in this regard, the valve/filter element material has a pore rating rather than merely characterizing same by pore size. In the preferred form, the pore rating of the valve/filter element is about 0.5 microns. This pore rating should be sufficient to entrap microorganisms which may be found in a hospital environment in which the present invention is intended to be used. In addition to this preferable pore rating, the valve/filter element desirably prevents liquid from passing therethrough even with substantially high pressure differentials across the element. In particular, valve/filter element 60 should be capable of developing sufficiently high surface tension under liquid contact to serve as a barrier against liquid passage therethrough at pressure differentials across the element up to 14.7 psi (1,034 g/cm$^2$). In other words, even at a pressure differential of 14.7 psi (1,034 g/cm$^2$) across the valve/filter element, no liquid will be permitted to pass therethrough. Inasmuch as the standard atmospheric pressure condition is about 14.7 psi, (1,034 g/cm$^2$) this valve/filter element should be capable of withstanding full vacuum conditions thereacross under standard atmospheric pressure levels. However, most hospital suction generating sources only apply a pressure gradient of about 5 psi (352 g/cm$^2$). Therefore, there normally would be a considerable margin of safety whereby liquid will be prevented from passing through the valve/filter element under the types of pressure gradient generated by typical hospital suction devices. On the other hand, the valve/filter element can be chosen to withstand a pressure gradient as high as 21 psi (1,476 g/cm$^2$).

Smoke filter 65 is preferably a thin porous sheet which includes a plurality of bores 66 therethrough illustrated in FIG. 4 in graphic form. Those skilled in the art will recognize that pores 66 may not extend straight through the thickness of the prefilter. It is the purpose of the smoke filter to filter the smoke so that it cannot contact and clog the element 60. The smoke filter is preferably a hydrophilic non-woven structure having a pore rating of about 0.5 microns. The smoke filter should be thick enough to trap and hold the solid and liquid components of the smoke without clogging. It should be noted that the function of filtering microorganisms is performed by the valve/filter element. Although the smoke filter means may also have this capability it is not necessary for the present invention to be functional. Also, in the event that the smoke filter means is inadvertently damaged so that its filtering capacity is impared, the valve/filter element will filter out microorganisms of about 0.5 microns and larger but the valve/filter element may no longer be protected from the components of smoke which can shut it down.

In order to prevent the moisture absorbed by the smoke filter from contacting valve/filter element 60 and shutting off the air flow, spacer 64 is provided. The primary purpose of spacer 64 is to separate element 60 and smoke filter 65. A wide variety of materials and constructions can perform the spacer function.

Figure 6:
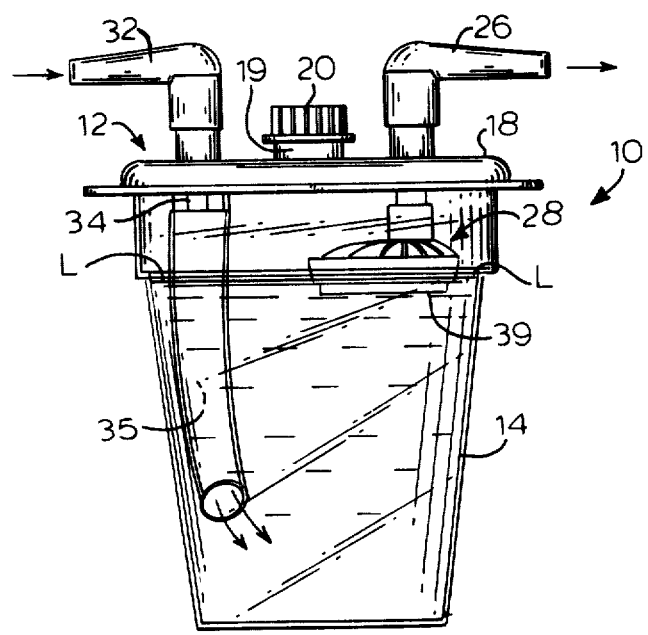
FIG. 6 is a side elevational view of the suction canister assembly of FIG. 1 illustrated with liquid therein rising to a level which would cause suction termination.

FIG. 6 depicts the preferred suction canister assembly of the present invention in use. Suction is applied through connector 26 and into receptacle 14 through valve/filter housing 28. The porous nature of the composite valve/filter assembly (inside housing 28) allows the suction forces to be transmitted through the valve/filter housing so that a negative pressure gradient is applied inside receptacle 14. As a result, liquid from the patient is drawn through connector 32 and through sheath 35 so that it is collected inside the receptacle. As long as the suction is applied and the level of liquid inside the receptacle remains low, the negative pressure gradient remains, thereby pulling more liquid into the receptacle. During this suction process while liquid is filling the receptacle, smoke, air and other gases, already in the receptacle or entering through sheath 35, are filtered when they pass through the smoke filter and the valve/filter element hereinabove described. Accordingly, particulate matter, including bacteria, traveling from the patient into the receptacle is filtered and collected primarily on the valve/filter element. Smoke, including that generated by the use of surgical tools such as lasers and electric knives, is filtered and collected primarily on the smoke filter.

Therefore, when using the above valve/filter assembly contamination of the vacuum pump (which is not a disposable item) and the environment surrounding the vacuum pump is also prevented. Once liquid level L inside the receptacle reaches a certain height, it passes through the open framework construction of lower portion 39 of the valve/filter housing. As soon as the liquid completely contacts the valve/filter element within, no liquid will pass through the element. Moreover, the liquid contacting the valve/filter element will also close off the vacuum which had been applied to the inside of the receptacle. In this regard, no further liquid can be drawn into the receptacle since the valving aspects of the valve/filter element effectively close off the negative pressure gradient which had been applied. Once this occurs, the attendant disconnects the suction canister assembly from the suction source and from the tubing to the patient.

Figure 7:
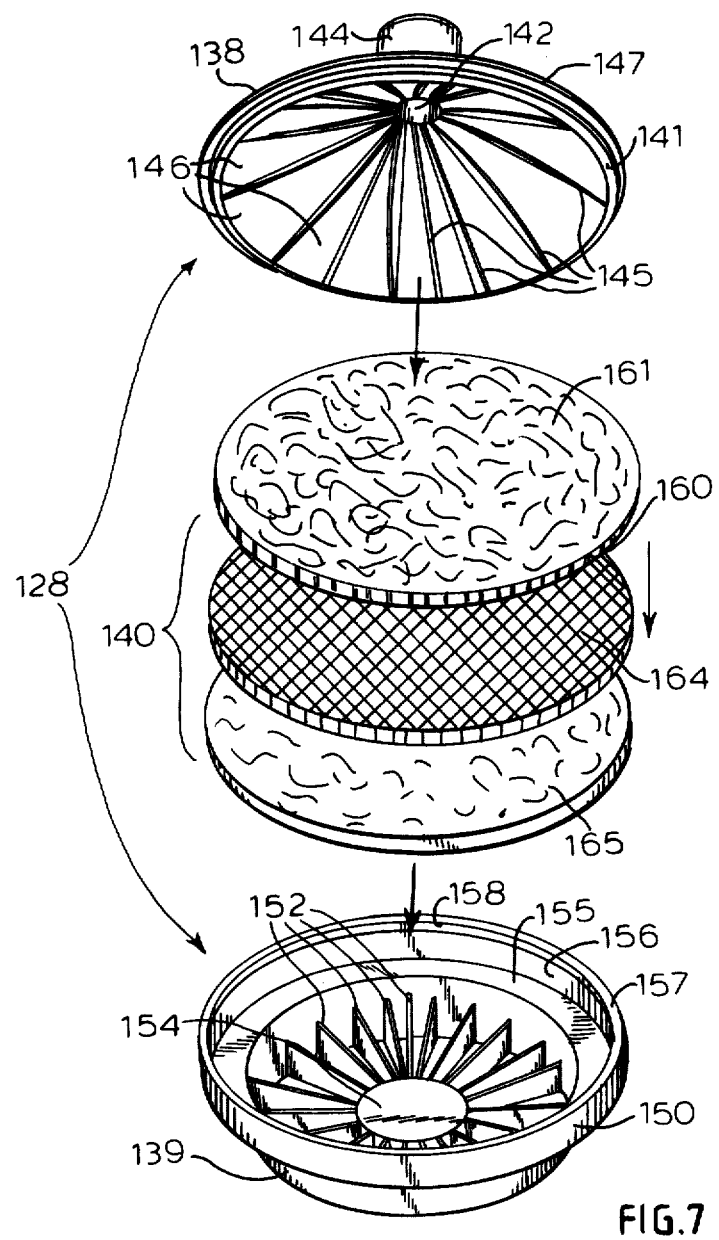
FIG. 7 is an exploded perspective view of the valve filter housing assembly of an alternative embodiment of the present invention.

FIG. 7 shows an alternative embodiment of the present invention. This embodiment is similar to the previously described embodiment except that all of the elements of a valve/filter structure 140 are not laminated together. A smoke filter 165 and a spacer 164 are both separate components and constructed as previously described. A backing sheet 161 and a valve/filter element are laminated together and constructed as previously described. A valve filter housing 128 includes an upper portion 138 and a lower portion 139. Upper portion 138 includes a generally planar surface 141 and a circular rim 147 defining an outside diameter. A hole 142 extends through the planar surface, and is defined by an upwardly extending post 144. This post is connectable to lower post 25 on the exterior side of cover 18 so that the inside of housing 128 will be in fluid communication with the suction opening 22. On the interior side of planar surface 141 is a plurality of ribs 145 spaced from each other and preferably extending radially from hole 142 and terminating at the planar surface. Between the adjacent ribs are channels 146, each channel being in fluid communication with hole 142. Lower portion 139 is substantially cylindrically-shaped including a cup portion 150 with a flat top rim 157 and a radial inwardly facing rib 158. Also included are an annular interior side wall 156 and a flat circular support ledge 155. The bottom surface of lower portion 139 is defined by a plurality of spaced, radially directed spokes 152 connected at their interior ends to a hub 154.

In assembly, backing sheet 161 with valve/filter element 160 attached is connected to planar surface 141 by heat sealing, adhesive or other suitable means. Smoke filter 165 is then placed in lower portion 139 so that it rests on ledge 155 and then spacer 164 is placed on top of the smoke filter. Upper portion 138 is now placed in lower portion 139 trapping the smoke filter and the spacer between support ledge 155 and planar surface 141 to which the element and backing sheet are joined. The housings are dimensioned so that rim 147 of the upper portion has a larger diameter than the circle described by inwardly facing rib 158. Accordingly, rim 147 is forced past rib 158 in a snap-fit arrangement. After the snapfit assembly is effectuated the space between ledge 155 and planar surface 141 is smaller than the combined thickness of the elements in valve/filter structure 140 thus trapping those components in a relationship which forms an air-tight seal around the periphery of the smoke filter and the spacer. Accordingly all gases entering the lower housing travel through the valve/filter structure and not around it. It will be apparent to one skilled in the art that numerous constructions could be used to join the upper portion and the lower portion of the housing while simultaneously containing the loose filter components and that the snap-fit arrangement described above is exemplary of these many possible variations. Also, it is within the purview of this embodiment to include a structure wherein the valve/filter element and the backing sheet are not attached to the upper housing portion but are secured upon assembly of the housing portions. It is also within the purview of this invention to include embodiments which do not include a backing sheet.

Figure 8:
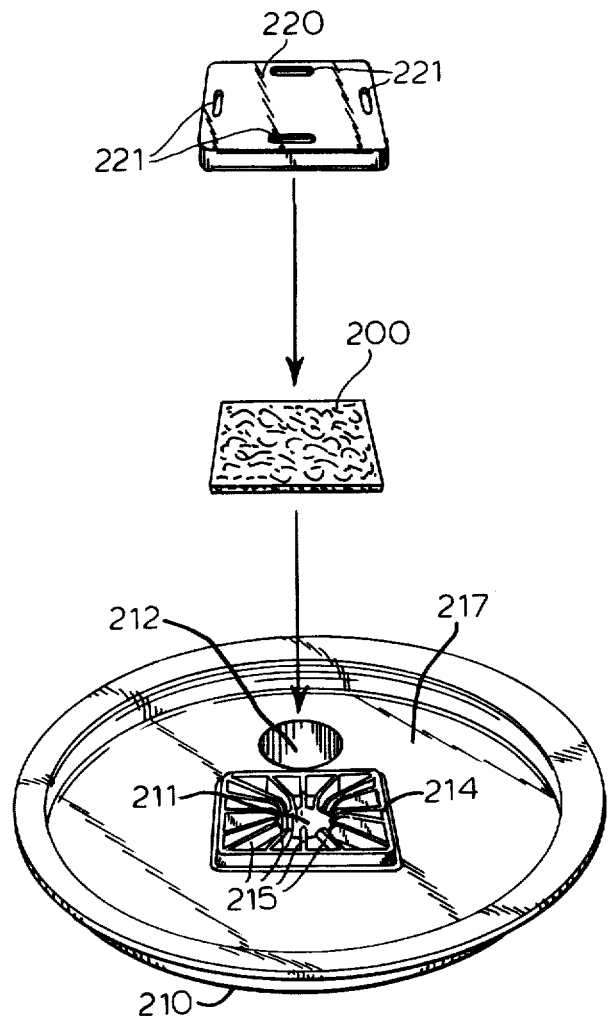
FIG. 8 is an exploded perspective view of the cover assembly of another alternative embodiment of the present invention.
Figure 9:
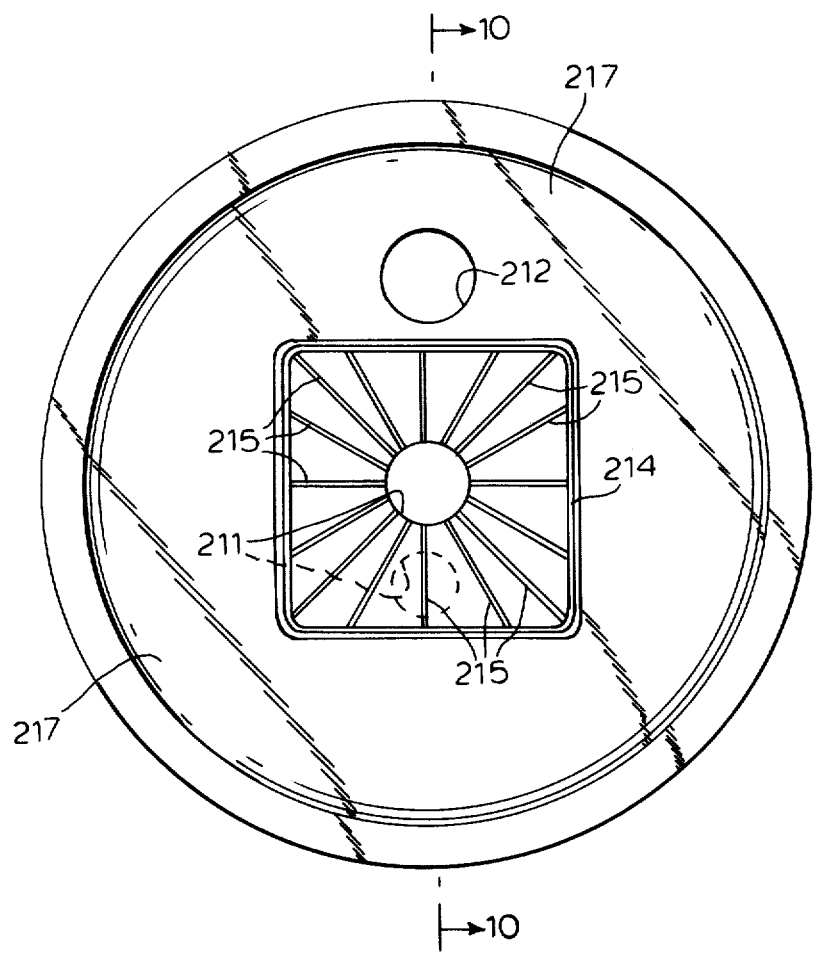
FIG. 9 is a bottom plan view of the cover of FIG. 8.

FIGS. 8, 9 and 10 show another alternative embodiment of the present invention. This embodiment is similar to the previously described embodiments except that the separate housing portions are eliminated and a composite valve/filter assembly 200 is attached directly to cover 210. The cover includes a suction opening 211 adapted to communicate with a source of vacuum and a liquid passage opening 212 adapted to communicate with a source of fluids to be collected in the receptacle (not shown). A raised planar mounting surface 214 provides a surface onto which the composite valve/filter assembly is mounted. A plurality of raised ribs 215 extends inwardly from the mounting surface and terminates near the suction opening. The raised ribs define a plurality of channels 216 which are located between the ribs. Each channel is in fluid communication with suction opening 211. It should be noted that it is not necessary for the suction opening to be centrally located for all of the channels to be in fluid communication therewith. An alternate position for the suction opening is shown with phantom lines in FIGS. 9 and 10. The raised ribs function to support the composite valve/filter assembly against forces in the vacuum direction and to provide a path for the gases to travel from the composite valve/filter assembly to the suction opening. To perform these functions it is preferred that the ribs be at or below the height of planar mounting surface 214. Ribs 215 which rise to the height of the planar mounting surface may also provide surface onto which the composite valve/filter assembly can be mounted.

Composite valve/filter assembly 200 includes the components previously described and shown in FIG. 4. However, in the embodiment of FIGS. 8-10, the composite valve/filter assembly is cut to the square shape described by mounting surface 214. It should be noted that it is within the purview of this invention to include a wide variety of mounting surface and composite valve/filter assembly shapes with the circular and square shapes described herein being exemplary of the many possible variations. The surface of the composite valve/filter assembly containing a backing sheet 201 is attached to the mounting surface 214 by the use of adhesive, ultrasonic welding or other suitable means. The seal provided should be airtight so that gases passing through the suction opening from the receptacle will pass through composite valve/filter assembly 200 and not around it. In the instant embodiment a splash shield 220 is provided to protect the composite valve/filter assembly from splashing fluid while providing apertures 221 to allow gases to pass freely from the receptacle through the valve/filter structure. Splash shield 220 may be held in position against an interior surface 217 of the cover by a wide variety of means including adhesive, ultrasonic welding, heat sealing and cooperating structure contained on the cover and the splash shield.

Some non-woven fabrics are suitable for backing sheet 61, 161 and 201 inasmuch as they are porous and can be made very thin, while strong. In this respect, and although other materials may be chosen, such non-woven material may be selected from the group of materials consisting of polypropylene, polyethylene and polyester. On the other hand, suitable materials for the valve/filter element, satisfying the above-noted criteria, are polymeric materials selected from polytetrafluoroethylene, polyester, polyvinylchloride, polypropylene, polyethylene and the like, preferably ranging in thickness of from about 0.003 to 0.010 inches (0.08 to 0.25 mm). Such laminated composite structures of valve/filter element and backing sheet as just described are available from W. L. Gore and Associates, Inc. of Elkton, Md., and are sold as GORE-TEX MEMBRANE PRODUCTS (as heretofore mentioned). The preferred valve/filter element is polytetrafluoroethylene, whereas the preferred backing sheet is a non-woven polypropylene. The composite thickness of preferred valve/filter element and backing sheet is approximately 0.008 inches (0.2 mm). A preferred pore rating is 0.5 microns, with the valve/filter element capable of withstanding a pressure differential across of up to 21 psi (1,476 g/cm$^2$) before any liquid will pass therethrough. However, gases will readily pass through this valve/filter element, but the pore rating should prevent most bacteria from passing through this element.

A wide variety of materials and constructions are suitable for spacer 64. The structure should be non-wetting and non-absorbing so that moisture trapped within the prefilter will not readily transfer across the spacer to contact the valve/filter element. Spacer 64 should be capable of being laminated to both the smoke filter and the valve/filter element. Woven or non-woven fabrics are suitable for spacer 64 with 4 to 8 mil (0.1 to 0.2 mm) non-woven polypropylene being preferred. However, thicker spacers in the range of 37 to 67 mils (0.94 to 1.7 mm) have been found to be effective. It should be noted that a thicker spacer will reduce the potential for filtered matter to transfer from the smoke filter to the valve/filter element at the expense of a greater pressure drop across the spacer. In the alternative embodiment of FIG. 7, in which spacer 164 is not laminated to the smoke filter or to the valve/filter element, an even larger variety of materials and constructions is available for use since there is no requirement that the spacer be laminatable to other components. Mechanical screen-like spacers are desirable since they can be made thicker while causing only negligible pressure drop across the valve/filter structure 140. It is preferred that spacer 164 be formed of an extruded polypropylene screen 17 to 23 mils (0.43 to 0.58 mm) thick with a strand count of approximately 11 strands per inch (4.3 strands/cm) in a first direction and 15 strands per inch (5.9 strands/cm) in a direction perpendicular to the first direction.

It is preferred that smoke filter 65 of the preferred embodiment and smoke filter 165 of the alternate embodiment of FIG. 7 be constructed of non-woven fiberglass sheet having a thickness of 10 to 15 mils (0.25 to 0.38 mm) and a basis weight of 12.9 to 13.9 pounds/100 ft$^2$ (63 to 67.9 kg/100 m$^2$) and a density of 0.072 to 0.083 pounds/in$^3$ (1986 to 2291 kg/m$^3$). Non-woven fiberglass smoke filter material as just described is available from Whatman Laboratory Products, Inc., Clifton, N.J., and sold as Whatman 934AH glass fiber sheet. The thickness of the smoke filter may be optimized based on specific conditions of use. A thicker smoke filter, even larger than the preferred thickness, may be chosen where it is desirable to increase smoke filtering capacity at the expense of a larger pressure drop across the smoke filter. This thicker smoke filter may be acceptable in applications where there is a particularly strong source of vacuum and minimal amounts of tubing and other components, such as valves, which tend to cause pressure drops, between the vacuum source and the liquid to be collected in the canister.

During assembly of composite valve/filter assembly 40 into housing 28, it is preferred to place the valve/filter structure so that smoke filter 65 faces downwardly or toward lower portion 39. In this way, smoke will contact the smoke filter first. Also, it is preferred that all other embodiments of the present invention be assembled with the smoke filter facing downwardly so that the smoke will contact the smoke filter first. Although not specifically shown in the drawings it should also be pointed out that composite valve/filter assembly 40 can be used in the housing assembly without lower portion 39 attached. Here again, composite valve/filter assembly 40 is secured directly to upper portion 38, serving as a support member, with smoke filter 65 facing downwardly.

Although many materials may be selected for the various components of the present invention, since the suction canister assembly is intended to be disposable, rigid plastic materials are preferably used. While sizes and shapes of the various components may vary according to design or choice, a typical valve/filter assembly in the present invention has a flow area for filtration purposes of approximately 3 square inches (19.4 cm$^2$). Also, of the total surface area of the valve/filter element, between 50% and 90% of the total surface area may include pores.

Thus, it can be seen that the present invention provides a suction canister assembly with a unique, combined valve and filter feature. The filter not only filters out particulate matter, but also filters bacteria from air or gases passing through the suction canister assembly as well as smoke including that generated by surgical tools such as lasers and electric knives. On the other hand, liquid contact of this element serves as a valve to not only control liquid overflow in the canister assembly, but also to close off suction into the canister assembly so that no more liquid can be collected therein.

What is claimed is:

1. A medical suction canister assembly for use in the aspiration of body fluids during cauterization or other smoke producing surgical procedures comprising:
    a cup-shaped receptacle having an open mouth portion and an opposed bottom wall;
    a cover sealably connected to said receptacle over said mouth portion, said cover having a suction opening therethrough for communicating with a source of vacuum applied to the exterior side of said suction opening, and having a liquid passage opening therethrough for communicating with a source of liquid exterior to said canister so that liquid is passable therethrough to enter said receptacle under suction conditions provided through said suction opening by said vacuum source, said cover having an upper housing portion projecting downwardly from said cover into said receptacle and terminating at a generally planar surface, said upper housing portion surrounding said suction opening and defining an interior portion in fluid communication with said suction opening, said planar surface adapted to be substantially parallel to the free upper surface of liquid which enters said receptacle;
    a unitary shut-off valve/filter element positioned adjacent to and contacting said planar surface and adapted to be contacted by liquid in said receptacle which rises to a predetermined level, said element adapted to lie substantially parallel to the free upper surface of liquid which enters said receptacle when said bottom wall rests on a substantially horizontal surface, said element being porous with a maximum pore rating of about 0.5 microns for filtering particulate matter including microorganisms from gas passing therethrough, said element capable of developing sufficiently high surface tension under liquid contact to serve as a barrier against liquid passage therethrough at pressure differentials across said element up to 14.7 psi, said element adapted to terminate suction through said suction opening at suction pressures up to 14.7 psi when liquid rises in said receptacle to completely cover said element, said element lying within a single suction path extending only from the interior of said receptacle to said suction opening so that all gases are exchanged between said receptacle and said suction opening through said element;
    smoke filter means for filtering solids and liquids contained in smoke for preventing said element from terminating suction before said element is contacted by liquid in said receptacle, said smoke filter means being positioned adjacent to said filter element on the side opposite said planar surface facing the interior of said receptacle;

spacer means for substantially preventing filtered matter collected by said smoke filter means from migrating to said filter element, said spacer means interposed between said filter element and said smoke filter means; and a lower housing including a side wall and a bottom portion defining an interior cavity, a generally planar shoulder extending inwardly from said side wall, said side wall being attached to said upper housing portion and positioned so that said planar surface and said shoulder are in a substantially parallel relationship holding said filter element, said spacer means and said smoke filter means therebetween in an air-tight seal around the periphery thereof, said bottom portion having a plurality of apertures adapted to allow gases to flow freely therethrough.

2. The suction canister assembly of claim 1 wherein said upper housing portion is removably connected to said cover.

3. The suction canister assembly of claim 1 wherein said upper housing portion is fixedly connected to said cover.

4. The suction canister assembly of claim 1 wherein said upper housing and said cover are integrally constructed.

5. The suction canister assembly of claim 1 further comprising a thin porous backing sheet laminated to said filter element on the side of said filter element facing said planar surface, said sheet adapted to provide stability to the composite structure of said filter element and said sheet, said backing sheet adapted to be attached to said planar surface.

6. The suction canister assembly of claim 5 wherein said backing sheet is a thin membrane.

7. The suction canister of claim 6 wherein said backing sheet is made of non-woven material selected from the group of materials consisting of polyester, polyethylene and polypropylene.

8. The suction canister assembly of claim 5 wherein said backing sheet is fixedly attached to said planar surface.

9. The suction canister assembly of claim 5 wherein said spacer means is laminated to said filter element on the side opposite said backing sheet and said smoke filter means is laminated to said spacer means.

10. The suction canister of claim 9 wherein said backing sheet is fixedly attached to said planar surface.

11. The suction canister assembly of claim 1 wherein said filter element is a thin membrane having a thickness of between 0.003 and 0.010 inches.

12. The suction canister of claim 1 wherein said filter element is made of polymeric material selected from the group consisting of polytetrafluoroethylene, polyester, polyvinylchloride, polypropylene and polyethylene.

13. The suction canister of claim 1 wherein said smoke filter means includes a non-woven fiberglass sheet having a density within the range of about 124 to 143 pounds per cubic foot and a maximum pore rating of about 0.5 microns.

14. The suction canister of claim 13 wherein said fiberglass sheet has a thickness within the range of about 10 to 15 mils.

15. The suction canister of claim 9 wherein said spacer means is made of non-woven polypropylene.

16. The suction canister assembly of claim 1 further comprising fluid channel means in said upper housing portion for preventing said filter element from collapsing under the suction forces.

17. The suction canister assembly of claim 16 wherein said fluid channel means comprises a plurality of spaced ribs within said interior portion, said ribs projecting downwardly from said cover into said receptacle and extending no further than said planar surface, a channel being recessed between adjacently lying ribs and in fluid communication with said suction opening.

18. A medical suction canister assembly for use in the aspiration of body fluids during cauterization or other smoke producing surgical procedures comprising:

a cup-shaped receptacle having an open mouth portion and an opposed bottom wall;

a cover sealably connected to said receptacle over said mouth portion, said cover having a suction opening therethrough for communicating with a source of vacuum applied to the exterior side of said suction opening, and having a liquid passage opening therethrough for communicating with a source of liquid exterior to said canister so that liquid is passble therethrough to enter said receptacle under suction conditions provided through said suction opening by said vacuum source, said cover having an upper housing portion projecting downwardly from said cover into said receptacle and terminating at a generally planar surface, said upper housing portion surrounding said suction opening and defining an interior portion in fluid communication with said suction opening, said planar surface adapted to be substantially parallel to the free upper surface of liquid which enters said receptacle;

a unitary shut-off valve/filter element connected to the interior side of said suction opening lying within a single suction path extending only from the interior of said receptacle to said suction opening so that all gases are exchanged between said receptacle and said suction opening through said element, said element adapted to lie substantially parallel to the free upper surface of liquid which enters said receptacle when said bottom wall rests on a substantially horizontal surface, said element oriented within said receptacle to be contacted by liquid in said receptacle which rises to a pre-determined level, said element being porous with a maximum pore rating of about 0.5 micron for filtering particulate matter including microorganisms from gas passing therethrough, said element capable of developing sufficiently high surface tension under liquid contact to serve as a barrier against liquid passage therethrough at pressure differentials across said element up to 14.7 psi, said element being laminated to a thin porous backing sheet adapted to provide stability to the composite structure of said element and said sheet, said composite structure connected to said planar surface so that said element faces toward the interior of said receptacle so as to be contacted by liquid therein, said element adapted to terminate suction through said suction opening at suction pressures up to 14.7 psi when liquid rises in said receptacle to completely cover said element;

smoke filter means for filtering solids and liquids contained in smoke for preventing said element from terminating suction before said element is contacted by liquid in said receptacle, said smoke filter means being positioned adjacent to said filter element on the side opposite said planar surface facing the interior of said receptacle; and spacer means for substantially preventing filtered matter collected by said smoke filter from migrating to said filter element, said spacer means interposed between said filter element and said smoke filter means, said spacer means being laminated to said filter element on the side opposite said backing sheet, said smoke filter means being laminated to said spacer means.

19. The suction canister assembly of claim 18 further comprising splash shield means for substantially shielding said smoke filter means from liquid splashing within said receptacle when the liquid level in said receptacle is below said valve filter element, said splash shield means having a plurality of apertures adapted to allow gases to flow freely therethrough.

20. The suction canister assembly to claim 18 further comprising fluid channel means in said upper housing portion for preventing said filter element from collapsing under the suction forces.

21. The suction canister assembly of claim 20 wherein said fluid channel means comprises a plurality of spaced ribs within said interior portion, said ribs projecting downwardly from said cover into said receptacle and extending no further than said planar surface, a channel being recessed between adjacently lying ribs and in fluid communication with said suction opening.

22. The suction canister of claim 18 wherein said smoke filter means includes a non-woven fiberglass sheet having a density within the range of about 124 to 143 pounds per cubic foot and a maximum pore rating of about 0.5 microns.

23. The suction canister of claim 22 wherein said fiberglass sheet has a thickness within the range of about 10 to 15 mils.

24. A medical suction canister assembly for use in aspiration of body fluids during cauterization or other smoke producing surgical procedures comprising:

an enclosed receptcle having a first opening for providing suction to said receptacle and a second opening for drawing fluids, including liquids or gases, into said receptacle during suction and a bottom wall opposed from said first opening;

unitary shut-off valve/filter means associated with the interior side of said first opening lying within a single suction path extending only from the interior of said receptacle to said first opening so that all gases are exchanged between said receptacle and said first opening through said element, said element adapted to lie substantially parallel to the free upper surface of liquid which enters said receptacle when said bottom wall rests on a substantially horizontal surface, said valve/filter means being oriented within said receptacle to be contacted by liquid in said receptacle which rises therein, said valve/filter means being porous with a maximum pore rating of about 0.5 micron for filtering particulate matter including microorganisms from gas passing therethrough, said valve/filter means capable of developing sufficiently high surface tension under liquid contact to serve as a barrier against liquid passage therethrough at pressure differentials across said valve/filter means up to 14.7 psi, said valve/filter means adapted to terminate suction through said first opening when liquid rises in said receptacle to completely cover said element;

smoke filter means for filtering solids and liquids contained in smoke for preventing said element from terminating suction before said element is contacted by liquid in said receptacle, said smoke filter means being positioned adjacent to said valve/filter means on the side oposite the interior side of said first opening facing the interior of said receptacle; and connection means for securing said valve/filter means and said smoke filter means together in an air-tight arrangement so that gases leaving said suction canister must pass through said smoke filter means and said valve/filter means before passing through said first opening.

* * * * *